United States Patent [19]

McAdams et al.

[11] Patent Number: 5,914,891
[45] Date of Patent: Jun. 22, 1999

[54] SYSTEM AND METHOD FOR SIMULATING OPERATION OF BIOCHEMICAL SYSTEMS

[75] Inventors: Harley H. McAdams, Stanford; Adam P. Arkin, Half Moon Bay; Lucille Shapiro, Stanford, all of Calif.

[73] Assignee: Board of Trustees, The Leland Stanford Junior University, Palo Alto, Calif.

[21] Appl. No.: 08/860,585

[22] PCT Filed: Jan. 19, 1996

[86] PCT No.: PCT/US96/00780

§ 371 Date: Jun. 11, 1997

§ 102(e) Date: Jun. 11, 1997

[87] PCT Pub. No.: WO96/22574

PCT Pub. Date: Jul. 25, 1996

Related U.S. Application Data

[63] Continuation-in-part of application No. 08/375,958, Jan. 20, 1995, abandoned.

[51] Int. Cl.⁶ ........................................................ G06F 17/18
[52] U.S. Cl. ............................................................. 364/578
[58] Field of Search ............................... 364/578, 528.01; 434/278; 436/183; 395/500, 680

[56] References Cited

U.S. PATENT DOCUMENTS

| | | | |
|---|---|---|---|
| 4,855,931 | 8/1989 | Saunders | 364/499 |
| 5,260,882 | 11/1993 | Blanco et al. | 364/499 |
| 5,434,796 | 7/1995 | Weininger | 364/496 |
| 5,446,870 | 8/1995 | Hinsberg, III et al. | 395/500 |
| 5,826,065 | 10/1998 | Hinsberg et al. | 395/500 |

FOREIGN PATENT DOCUMENTS

PCT/US96/00780  5/1996  WIPO .

OTHER PUBLICATIONS

Tchuraev, "A New Method for the Analysis of the Dynamics of the Molecular Genetic Control Systems. I. Description of the Method of Generalized Threshold Models", J. theor. Biol. (1991), 151, pp. 71–87.

Kraus et al., "Structured Biological Modelling: a method for the analysis and simulation of biological systems applied to oscillatory intracellular calcium waves", BioSystems, 27(1992) pp. 145–169.

(List continued on next page.)

*Primary Examiner*—Kevin J. Teska
*Assistant Examiner*—Thai Phan
*Attorney, Agent, or Firm*—Flehr Hohbach Test Albritton & Herbert LLP

[57] ABSTRACT

A system and method for simulating the operation of biochemical networks includes a computer having a computer memory used to store a set of objects, each object representing a biochemical mechanism in the biochemical network to be simulated. Most objects have one or more associated signals, representing quantities or concentrations of associated proteins, positions of associated molecules, or other information concerning the state of a biochemical network. Each object has an associated set of methods. These methods include methods for determining reaction probabilities for biochemical reactions associated with the objects, and reaction simulation methods for simulating performance of those biochemical reactions. For a specified simulation time period, the operation of the biochemical network is simulated by executing at least a subset of the probability determination methods to determine reaction probabilities for at a subset of the biochemical reactions associated with the objects, selecting ones of the reaction simulation methods to execute in accordance with the determined reaction probabilities, and executing the selected ones of said reaction simulation methods. Execution of the selected reaction simulation methods causes associated ones of the signals to be updated. Output data representing values of selected ones of the signals is accumulated and presented.

16 Claims, 8 Drawing Sheets

OTHER PUBLICATIONS

Jacques Monod and Francois Jacob; General Conclusions: Teleonomic Mechanisms in Cellular Metabolism, Growth, and Differentiation; 1961; Cold Spring Harbor Symp on Quant Biol.; vol. 26; pp. 389–401.

Leon Glass, The Logical Analysis of Continuous, Non–linear Biochemical Control Networks; Aug. 22, 1972; pp. 103–129.

Rene Thomas; Regulatory Networks Seen as Asynchronous Automata: A Logical Description; Apr. 3, 1991; pp. 1–23.

Motoyosi Sugita; Functional Analysis of Chemical Systems in vivo using a Logical Circuit Equivalent. II. The Idea of a Molecular Automation; Nov. 5, 1962; pp. 179–193.

Rustem N. Tchuraev; A New Method for the Analysis of the Dynamics of the Molecular Genetic Control Systems. I. Description of the Method of Generalized Threshold Models; Sep. 15, 1990; pp. 71–87.

Elena I. Prokudina, Rustem Yu, Valeev and Rustem N. Tchuraev; A New Method for the Analysis of the Dynamics of the Molecular Genetic Control Systems. II. Application of the Method of Generalized Threshold Models in the Investigation of Concrete Genetic Systems; Sep. 14, 1990; pp. 89–110.

James L. Hargrove; Microcomputer–assisted kinetic modeling of mammalian gene expression; Sep. 1993; pp. 1163–1170.

Dennis Bray, Robert B. Bourret, and Melvin I. Simon; Computer Simulation of the Phosphorylation Cascade Controlling Bacterial Chemotaxis; May 1993; pp. 469–482.

Allen Hjelmfelt, Edward D. Weinberger, and John Ross; Chemical implementation of neural networks and Turing machines; Dec. 1991; pp. 10983–10987.

Allen Hjelmeflt, Edward D. Weinberger, and John Ross; Chemical implementation of finite–state machines; Jan. 1992; pp. 383–387.

Adam Arkin and John Ross; Computational Functions in Biochemical Reaction Networks; Aug. 1994; pp. 560–578.

M. Kaufman, J. Urbain and R. Thomas; Towards a Logical Analysis of the Immune Response; J. Theor. Biol (1985) 114; Academic Press Inc. (London); Aug. 10, 1984; pp. 527–561.

SYSTEM AND METHOD FOR SIMULATING OPERATION OF BIOCHEMICAL SYSTEMS

This application is a continuation-in-part of U.S. patent application Ser. No. 08/375,958, filed Jan. 20, 1995, entitled "System and Method for Simulating Operation of Genetic Circuits," which is abandoned now. U.S. patent application Ser. No. 08/375,958 is hereby incorporated by reference in its entirety.

The present invention relates generally to simulating the operation of existing and proposed networks of biochemical reactions or mechanisms, including genetic and non-genetic mechanisms or reactions, and particularly to a system and method of simulating the operation of biochemical systems using techniques similar to electrical circuit and logic circuit simulation techniques.

BACKGROUND OF THE INVENTION

The present invention provides a system and method for predicting the operation of existing and proposed networks of biochemical mechanisms, such as combinations of genetic sequences and biochemical mechanisms. In particular, a genetic sequence, or a combination of genetic sequences and other biochemical mechanisms can be modeled, using the present invention, as a set of interacting objects that operate as a biochemical circuit.

In this document the terms circuit, network and regulatory network shall be used interchangeably.

As will be explained below, biochemical networks or circuits can be modeled and simulated using bio-logic components in a manner that is analogous to the modeling of electrical circuits by electrical logic circuit components. Analysis of biochemical circuits using the present invention focuses on simulation at the "circuit logic" level.

Various types of biochemical mechanisms can be modeled at greater and lesser levels of biochemical detail by using different object models to simulate the operation of those mechanisms. In this way, simulations of biochemical circuits can be executed so as to focus on the signals (i.e., changing concentrations of molecules and chemicals that convey information) and accuracy levels of interest to the user.

By casting "bio-logic" networks in the framework of conventional switching circuits, we gain access to an enormous heritage of analysis and modeling techniques. In particular, switching circuit analysis techniques developed in the domain of electrical engineering are effective for analyzing some genetic circuits and may provide insights that are not as apparent from the biochemical perspective. One example is the central role that time delay and memory mechanisms play in determining the behavior of genetic control networks.

Intuitive analysis of large genetic regulator networks with positive and negative feedback loops is difficult. The simulation models of the present invention allow such analysis and make it possible to analyze altered genetic networks to predict mutant behavior. Furthermore, configuring well-characterized biological "components", such as those in the bacteriophage lambda genetic network, into new circuit configurations may provide access to new pharmacological strategies.

It is therefore a primary goal of the present invention to facilitate the analysis and network level design of biochemical circuits that comprise 10's to 100's of genes that control cellular events spanning minutes to hours.

Another goal of the present invention is to provide a set of reusable biochemical circuit simulation tools that can be easily rearranged to simulate the operation of a large variety of biochemical regulatory networks.

While borrowing from the circuit simulation techniques used in electrical engineering, the preferred embodiment of the present invention also simulates the stochastic fluctuations associated with biochemical regulatory signals. Stochastic fluctuations play an important role in biochemical networks. For instance, phenotypic diversity observed among individual cells within genetically uniform populations grown under identical conditions suggests that gene expression has a strong stochastic element. Through the use of various feedback mechanisms, genetic mechanisms can exhibit simultaneous stochastic gene expression and stable outcomes. However, even protein levels stabilized by autoregulatory feedback are found to have significant levels of random fluctuations. It is therefore a goal of the present invention to simulate the effect of stochastic fluctuations on biochemical networks in individual cells and to estimate the variation in network functioning and timing or phenotype distribution expected in a cell population.

SUMMARY OF THE INVENTION

In summary, the present invention is a system and method for simulating the circuit level behavior of biochemical networks. Any specified real or hypothetical biochemical network is represented by a configuration of biochemical reaction mechanisms including cellular machinery for transcribing and translating the information in genes to produce protein molecules, a variety of mechanisms to control the sequencing and timing of gene expression, and mechanisms to effect and control rearrangement, location, and access to genetic information stored in DNA (deoxyribonucleic acid), as well as other systems of coupled biochemical reactions.

BRIEF DESCRIPTION OF THE DRAWINGS

Additional objects and features of the invention will be more readily apparent from the following detailed description and appended claims when taken in conjunction with the drawings, in which:

DESCRIPTION OF THE PREFERRED EMBODIMENTS

Electrical versus Biochemical Circuits

Figure 1:
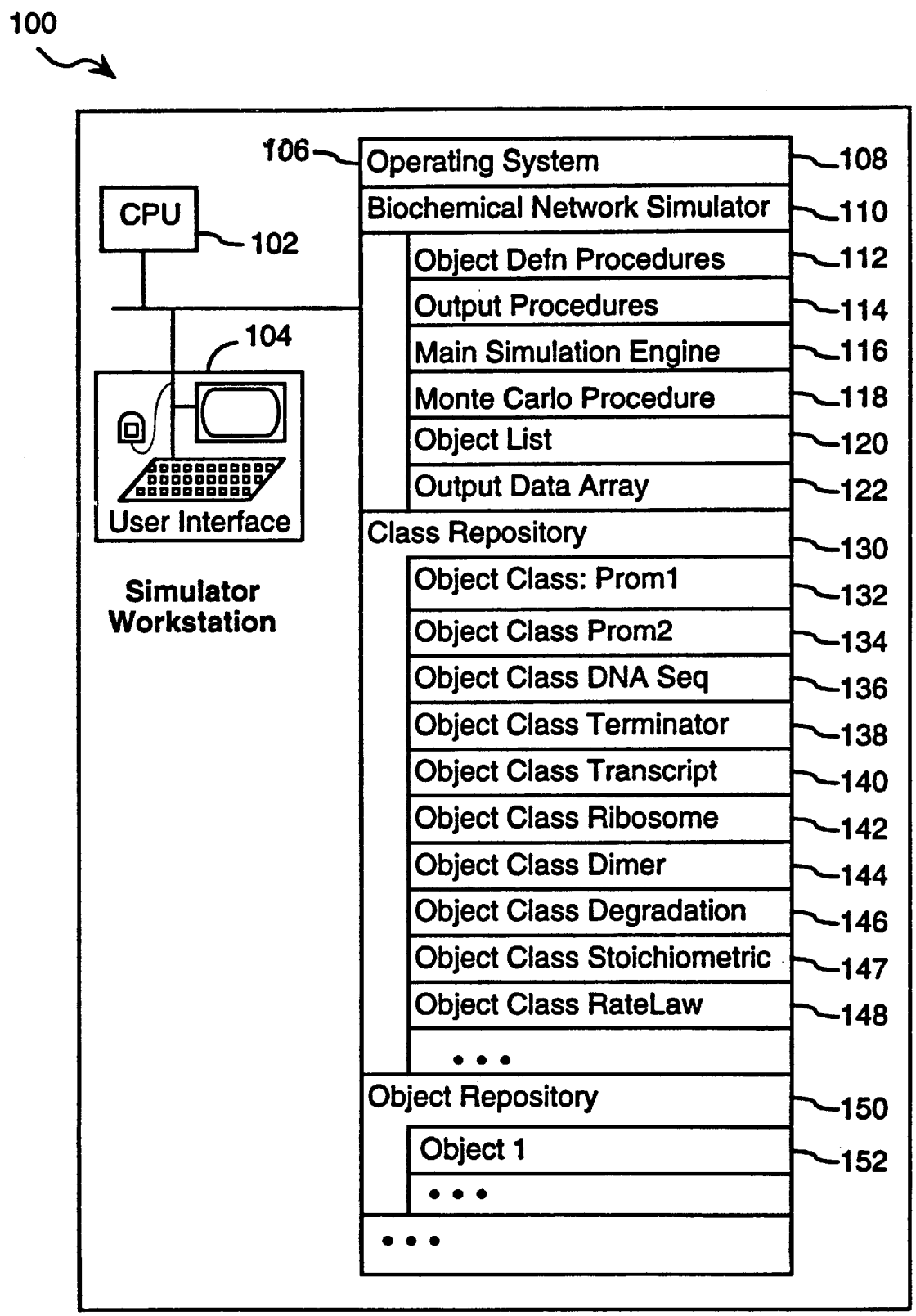
FIG. 1 is a block diagram of a preferred embodiment of a biochemical network simulator in accordance with the preferred embodiment of the present invention.

Since electrical engineers routinely describe and analyze networks of thousands of individually complex elements, it is instructive to consider parallels with genetic networks.

Although there is a great disparity in time scales between genetic control circuits and electronic control circuits, there are many parallels in their function. Electromechanical devices switch in small fractions of a second, and common transistor circuits can operate at more than $10^8$ cycles per second. In contrast, the switching rate in genetic control circuits is around $10^{-2}$ per second. Thus computer electronic switching rates are more than $10^{10}$ times faster than genetic switching rates. The connectivity of electrical circuits is determined by the conducting pathways between components. Similarly, a biochemical regulatory circuit is determined by connecting each signal's source to its site of action, but the connections are determined by the site-specific biochemical addresses of the protein signals. Transport is by free or constrained diffusion or by positively directed movement. The molecular signal may be modified or blocked between source and site of action by chemical reactions such as proteolysis or changes in phosphorylation state. Site-specific biochemical addressing permits many genetic logic circuits to operate in parallel without interference within the same small cell volume. Thus, the cell achieves high computational density in terms of logic operations/second/cc and the instantaneous amount of computation within any living organism is enormous in spite of slow component switching rates.

In logic simulators, electrical switching circuits are characterized as networks of idealized switching devices, i.e., devices with instantaneous transitions between states at precise times. However, practical electrical devices exhibit finite transition times and transient responses. The idealization of practical electronic devices permits simplified characterization of switching circuits based on Boolean logic while retaining the observed behavior of the system.

In circuit simulators, as opposed to logic simulators, electrical circuit networks are characterized using more complex models than the simple switching models used in logic simulators. The degree of accuracy of the simulation is governed by the complexity of the model used for each circuit element and the availability of accurate parametric measurements on real circuit elements for use with the circuit models. Often, accurate modeling of a circuit network as a whole requires only moderately accurate modeling of most of the network's circuit elements.

In a parallel manner, the present invention uses a Boolean gate representation of biochemical network elements whose actions are rapid relative to the overall biochemical network time constants, and uses more complex models for biochemical network elements whose actions are slower or which exhibit a more stochastic distribution of actions over time.

Glossary

To assist the reader, the following glossary of terms used in this document is provided.

Antitermination: an antitermination site is a site on a DNA strand at which RNAP can be antiterminated if a sufficient concentration of the necessary antiterminator proteins are present. Antiterminated RNAP is a complex of several proteins. Antiterminated RNAP passes through terminator sites with no or reduced attenuation, while RNAP that has not been antiterminated is stopped either completely or partially by terminator sites.

Bacteriophage: a virus that infects bacteria (same as phage).

Complex: a noncovalent association of molecules that function as a unit, often to implement a chemical processing mechanism. Examples includes the RNA polymerase (RNAP) transcription mechanism and the ribosome mechanism that translates transcripts to produce proteins.

cro: a protein that regulates the $P_L$, $P_R$, and $P_{RM}$ promoters in lambda phage.

Degradation Reactions: the proteolytic reactions that degrade various proteins.

Dimer: a compound of two proteins joined together via a dimerization reaction.

Eukaryotic cells: all types of cells that have a nucleus, including cells of higher organisms such as humans.

mRNA: message RNA, which is generated by transcription of a gene by RNAP traveling along a DNA strand on which the gene is located. Also called a transcript. Encodes information from a DNA sequence that is translated by ribosomes into proteins.

Phage (or Bacteriophage): a virus that only invades bacteria.

Prokaryotes: a bacterium (no nucleus).

Prokaryotic cells: cells of simple organisms such as bacteria that do not have a nucleus.

Promoter: a site on a DNA strand at which RNA polymerase (RNAP) binds to the DNA strand and initiates transcription when an open complex is formed. There are a large variety of promoter mechanisms with a corresponding large variety of control mechanisms for controlling the binding of RNAP to DNA strands at promoter sites. These different promotor mechanisms are modeled in the preferred embodiment by using different promoter objects with different object model methods for each type of promoter.

Proteases: enzymes that break down proteins.

Prophage: a phage that has integrated into the chromosome of a bacterial cell.

Ribosome: a complex of molecules that reads mRNA and translates the encoded information in the mRNA into a protein.

RNAP: RNA polymerase, the complex of molecules that travels along a DNA strand, transcribing the information encoded in the DNA strand into a mRNA strand (i.e., a transcript) that subsequently can be translated into protein by ribosome action.

Terminator: Terminators are sites on DNA strands at which transcription of RNAP along DNA will be stopped, either completely or partially. The action of termination sites is reduced or eliminated if the RNAP is "antiterminated" by the action of anti-termination molecules.

Transcription: the process of interpreting a gene's DNA code and synthesizing a message RNA molecule complementary to one strand of the double-stranded DNA molecule. RNAP does this.

Transcript: the mRNA strand or molecule produced when RNAP transcribes a stretch of DNA.

Translation: The process performed when a ribosome reads a RNA message (mRNA) and translates it to synthesize the corresponding protein.

Biochemical Network Simulator

Referring to FIG. 1, the biochemical network simulator 100 in the preferred embodiment is a computer workstation having a central processing unit (CPU) 102, a user interface 104, and memory 106, including both primary memory, typically called random access memory (RAM), and non-volatile secondary memory, typically magnetic or optical disk storage.

Memory 106 stores an operating system 108, preferably one providing support for object oriented programs;

a biochemical network simulator 110;

a class repository 130 for storing defined object classes, where each object class has the procedures required for modeling the operation of a particular biochemical mechanism; and an object repository 150 for storing objects, which are instances of the defined object classes, where each object can be used as a component of a biochemical network whose operation is to be simulated by the biochemical network simulator 110.

The biochemical network simulator includes a object definition procedures 112 for defining new types of objects that model various biochemical mechanisms;

output procedures 114 for storing, retrieving, and presenting results generated by the simulator;

a main simulation engine procedure 116;

a Monte Carlo procedure 118 for controlling the process by which a stochastic mechanism simulation is repeated multiple times and the results thereof are accumulated to show the predicted behavior of systems having multiple instances of the simulated biochemical network;

an object list 120 representing the biochemical network to be simulated; and an output data array 122 for storing a list of watched signals, and output data values for those watched signals.

The class repository 130 in a preferred embodiment includes the following object classes numerous promotor object classes (of which just two, Prom1 132 and Prom2 134, are shown) for simulating the operation of various types of promoters;

a DNA sequence object class 136 for simulating or representing a DNA sequence (also herein called a DNA strand);

a terminator object class 138 for simulating the operation of a terminator;

a transcript object class 140 for simulating the operation of a mRNA transcript generated when a RNAP complex transcribes a gene;

a ribosome object class 142 for simulating the operation of a ribosome that reads a mRNA transcript and translates the encoded information in the mRNA transcript into a protein;

a dimer object class 144 for representing the dimerization mechanism that converts pairs of proteins such as a pair of Cl molecules into a dimer, and vice versa, until a predefined equilibrium between dimers and monomers is achieved;

a protein degradation object class 146 for representing protease-based protein degradation mechanisms that degrade proteins in a cell;

a stoichoimetric object class 147 for representing chemical reactions whose operation can be represented by closed equations such as 2A+3B=2C, where A, B, and C represent specified molecules or chemicals; and a rate law object class 148 for representing chemical reactions whose operation is known from empirical observations but for which a closed equation representation is not known.

Users of the simulator 100 may at times need to define new object classes, which would then be added to the class repository 130. Defining new object classes will typically require the use of additional tools, not shown in FIG. 2, such as a C++ program editor and a C++ program compiler. One of the advantages of the preferred embodiment of present invention is that new object classes can be added to the simulator 100 without requiring recompilation or other changes to the other parts of the simulator 110.

Figure 2:
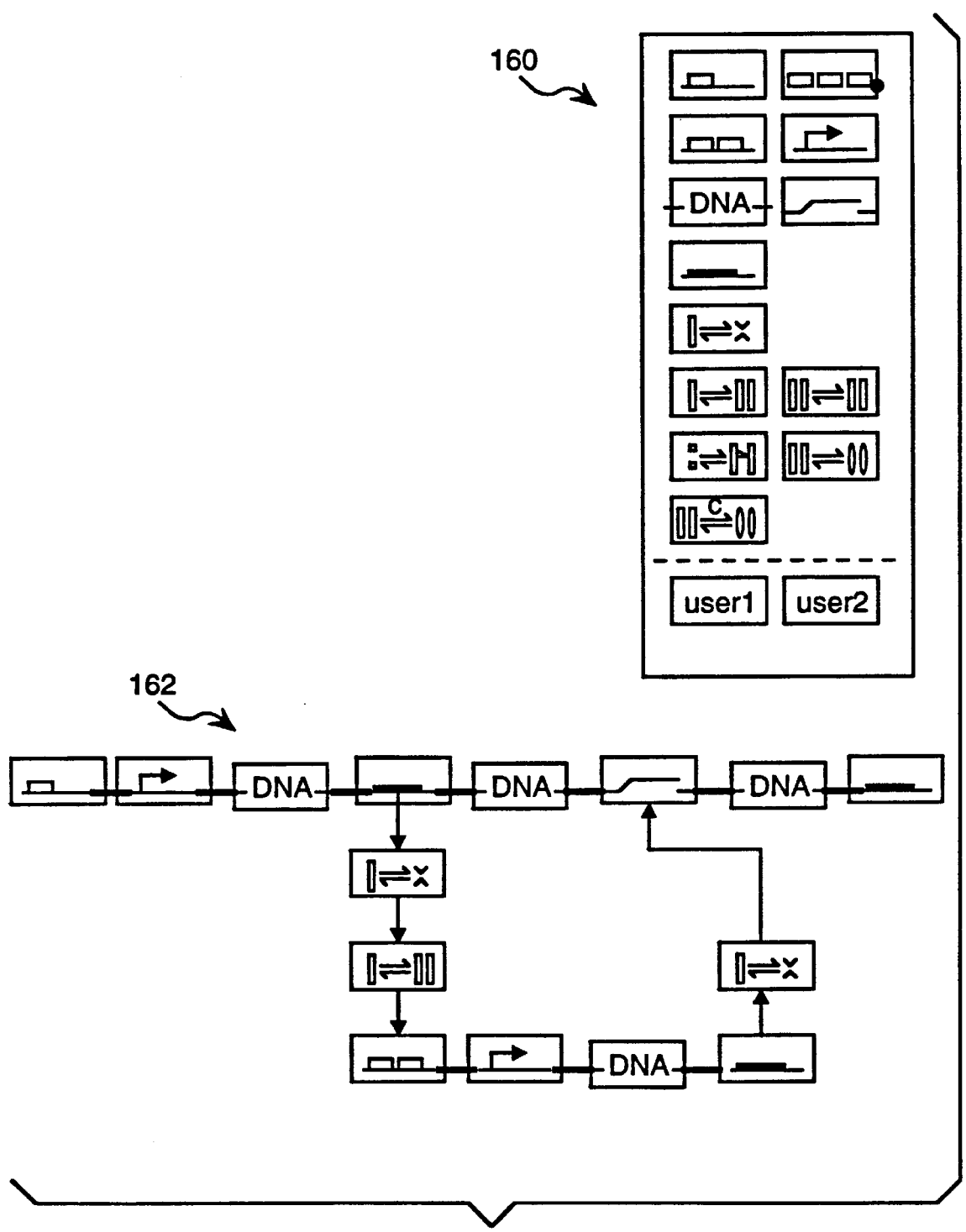
FIG. 2 is a schematic representation of a graphical user interface used to specify a biochemical network.

FIG. 2 shows a schematic representation of the graphical user interface used to specify a biochemical network. The objects represented in the graphical user interface are generated by the object definition procedures 112 (FIG. 1). The graphical user interface preferably provides a menu 160 of predefined objects as well as user defined objects. The user defines a biochemical network 162, such as an extended DNA sequence, by connecting a number of DNA strand objects, promoter objects, terminator objects, antiterminator objects and genes together (to correspond to the system being modeled), using a set of tools very similar to the tools found in standard computer drawing packages. This linked set of objects define the biochemical characteristics of a real or hypothetical DNA sequence. The biochemical network 162 defined by the user can also include objects representing other biochemical processes that are either not tied to specific DNA strand sites, or are other reaction types, such as dimerization and protein degradation. These other processes may take place in the cell cytoplasm or at localized sites in the cell, for example, at the cell membrane.

A set of objects can be combined to form larger user-defined objects.

Figure 3:
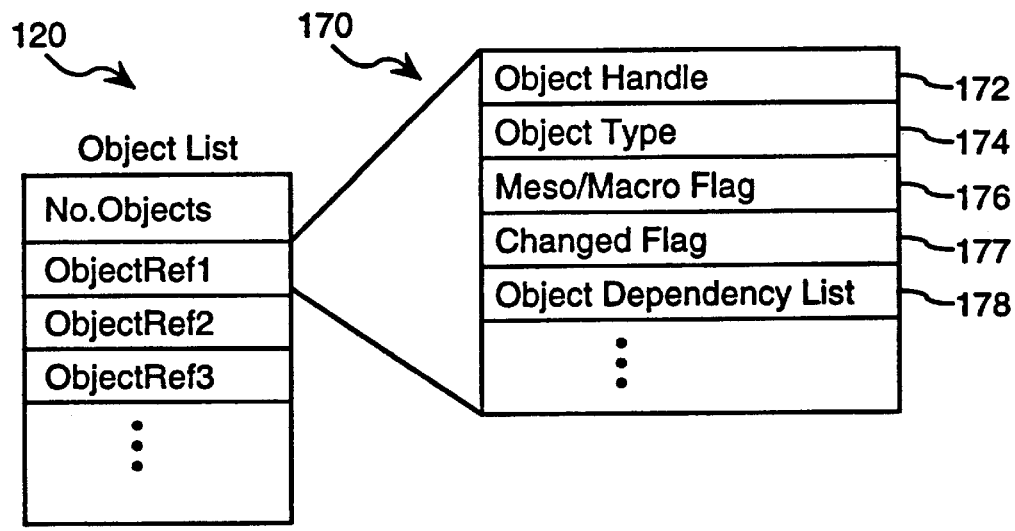
FIG. 3 is a block diagram of an "object list" data structure used in the preferred embodiment of the present invention.
Figure 4:
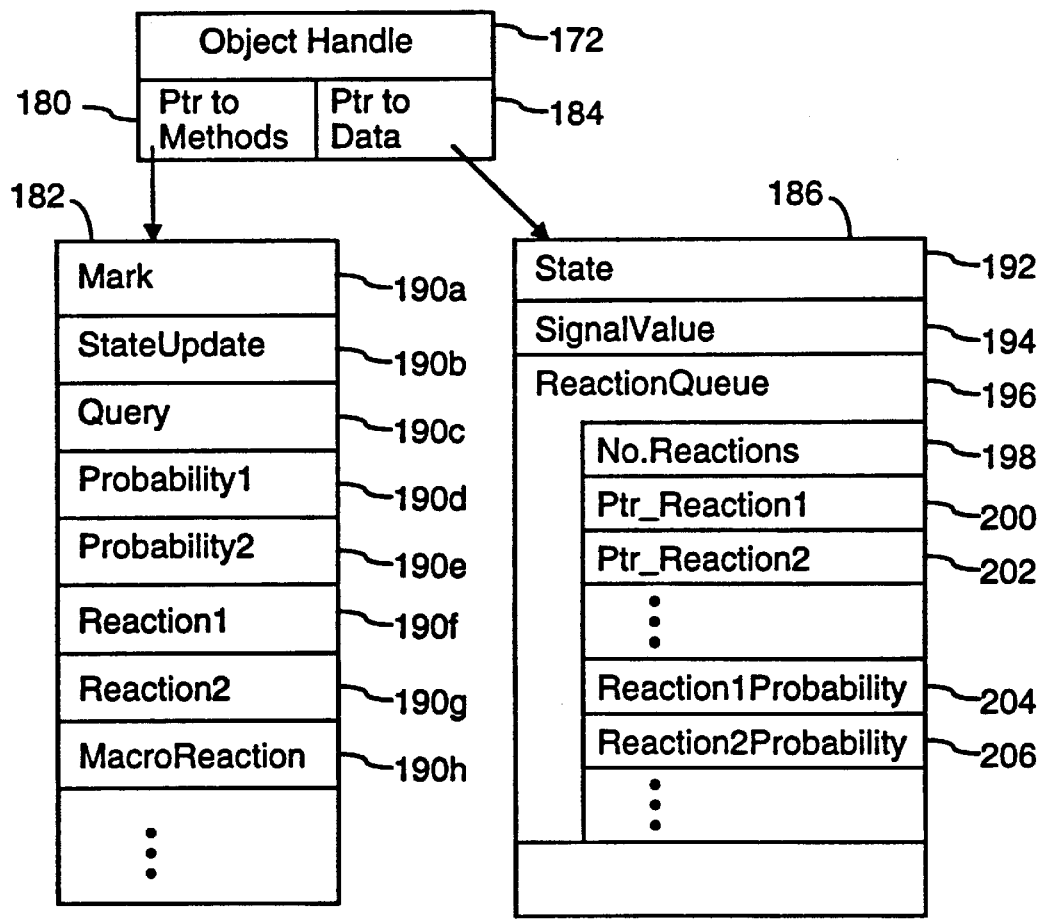
FIG. 4 is a block diagram of an object data structure used in the preferred embodiment of the present invention.

Referring to FIGS. 3 and 4, the internal data structures which represent the user defined biochemical network include an object list 120, listing all the objects in the defined network. Each object reference in the object list 120 points to an object instance 170, which includes an object handle 172, a field indicating the object's type 174, a "meso/macro" flag 176 indicating (as will be described in more detail below) how the object should be simulated during the next simulation time period, a "changed flag" 177, and an object dependency list 178.

Each object handle 172 includes a methods pointer 180 to a methods array 182 and a data pointer 184 to a data array 186. All objects of the same object type share the same methods array 182, which is part of the associated object class, because they all use the same methods (i.e., procedures) to update their state and simulate biochemical reactions. In the preferred embodiment, each object class includes the following methods:

an object "marking" method 190a, for determining whether the associated object will be treated as a mesoscopic or macroscopic reaction object. Mesoscopic objects model mechanisms or reactions where microscopic chemical fluctuations are important, or at least potentially important, and which need to be stochastically modeled. Macroscopic objects model mechanisms or reactions where such fluctuations are not important and whose output signals usually change relatively slowly over time. Each object class has its own Mark procedure for determining whether each object of that class should be treated as a mesoscopic or macroscopic object. For instance, the Mark procedure for some object classes may force all objects of the class to always be mesoscopic, while the Mark procedure of other object classes may have a threshold concentration value above which the object is treated as macroscopic object. The resulting meso/macro decision is stored in the object instance's meso/macro flag 176. The meso/macro flag 176 acts, in essence, as a method selector for updating the signal level associated with the object.

a StateUpdate method 190*b*, used primarily to determine the current state of multistate objects, such as a multisite promoter. A state is one of several discrete alternative configurations or chemical arrangements that a complex of molecules can be in. For single state objects, the StateUpdate procedure just returns a constant value. The resulting state value is stored in the State field 192 of the object instance's data array 186.

a Query method 190*c*, and a set of zero or more associated Probability methods 190*d*, 190*e*, for recomputing or updating the reaction probabilities associated with the object. The Query method for an object is called when any of the objects on which those reaction probabilities depend have been updated by a previous reaction. When an object has more than one associated possible reaction, a separate Probability method may be provided to compute the probability of each such possible reaction. As shown in FIG. 3, the data array 186 for an object with multiple possible reactions includes a "ReactionQueue" subarray 196. The ReactionQueue subarray 196 has a field 198 that specifies the number of different reactions that the object can perform, plus pointers 200, 202 to the methods for each of those different reactions. The probability values for all the possible reactions, as computed by the Probability methods 190*d*, 190*6e*, are stored in ReactionProbability fields 204, 206 in the ReactionQueue subarray 196. For objects having only a single associated reaction, the number of reactions specified by field 198 is "1", the Reaction Queue includes only a single ReactionProbability field, and the object class' methods array includes only a Query method 190*c* without any associated probability methods.

one or more Reaction methods 190*f*, 190*g* for simulating a reaction by an object instance. For instance, a reaction might be the movement of a RNAP complex (sometimes herein called a "RNAP molecule" for convenience) by one position down a DNA strand, or might be the combining of two protein molecules into a dimer. If an object class has multiple possible reactions, a similar number of reaction methods are provided. Generally, execution of the Reaction Method 190*f* results in the SignalValue 194 of the object being updated. In some cases, execution of the Reaction Method 190*f* may result in the generation of an object, the updating of other data values specific to the object's class, or the updating of the signal value or other data values for an object that is linked to the object whose Reaction method is being executed. For instance, when the execution of the Reaction method of a ribosome object results in the successful translation of a transcript into a protein molecule, the ribosome object is deleted, and the signal level of the associated gene object is increased by one protein to indicate an increased concentration of the protein.

a MacroReaction method 190*h*, for simulating a reaction by an object instance when the object is being simulated as macroscopic mechanism.

It is noted that a single object class can incorporate two more alternate reaction models, selectable on an object-by-object basis by the setting of one or more flags (typically by marking an appropriate checkbox when using the graphical user interface). For instance, for the RNAP motion model, a first model may take into account blocking of a RNAP molecule's motion by a preceding RNAP molecule on the same DNA strand, while a second model might neglect such blocking. In this way a single object class can be used to simulate the behavior of particular mechanisms or reactions at greater and lesser levels of detail in accordance with the user's model selections.

Simulation Procedure

Tables 1–5 contain pseudocode representations of the main simulation procedure, as well as examples of object methods called by the main simulation procedure. The pseudocode used in these appendices utilizes universal computer language conventions. While the pseudocode employed here has been invented solely for the purposes of this description, it is designed to be easily understandable by any computer programmer skilled in the art.

Figure 5A:
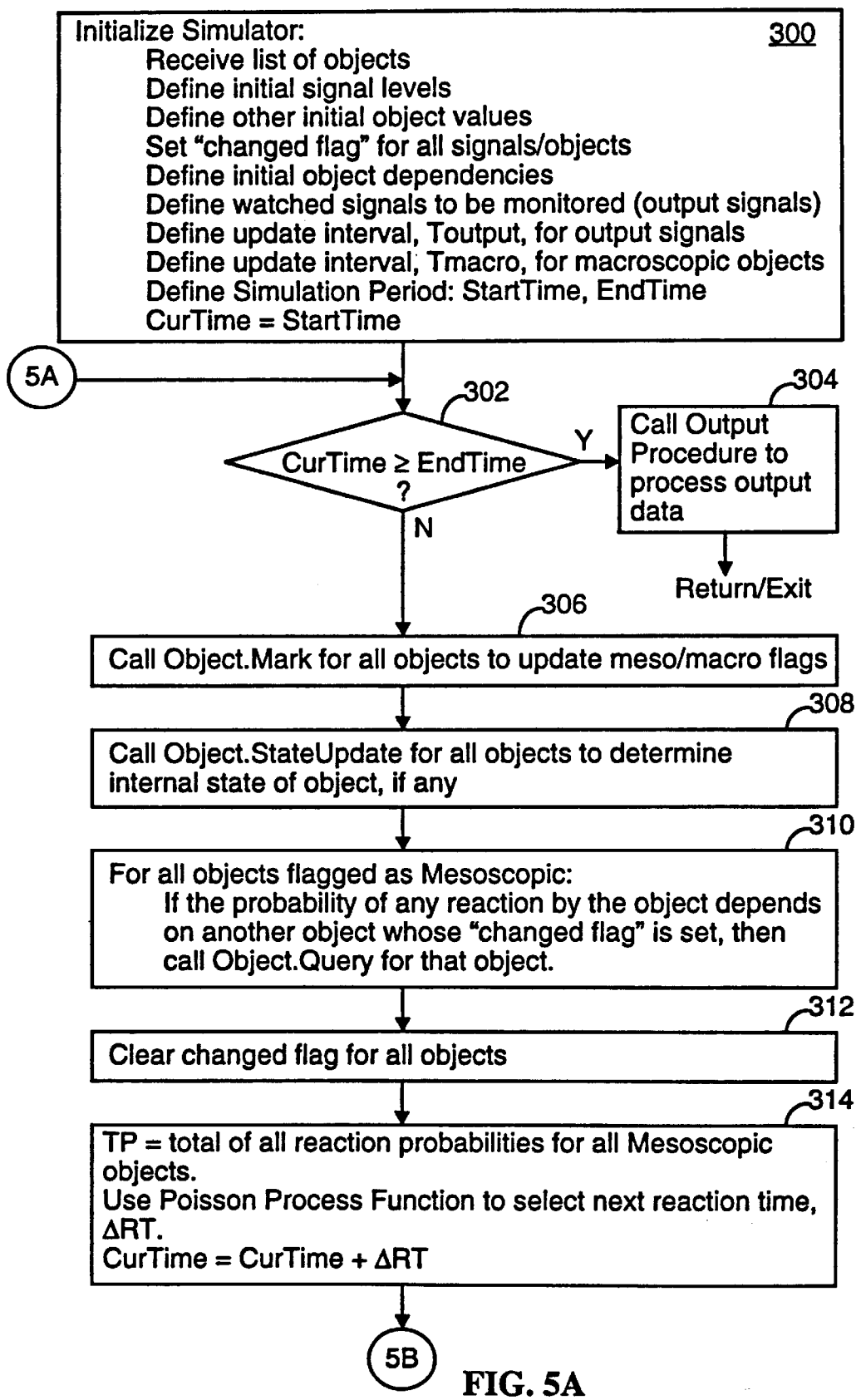
FIGS. 5, 5A, 5B is a flow chart of the simulation method used in the preferred embodiment of the present invention.
Figures 5, 5A, 5B:
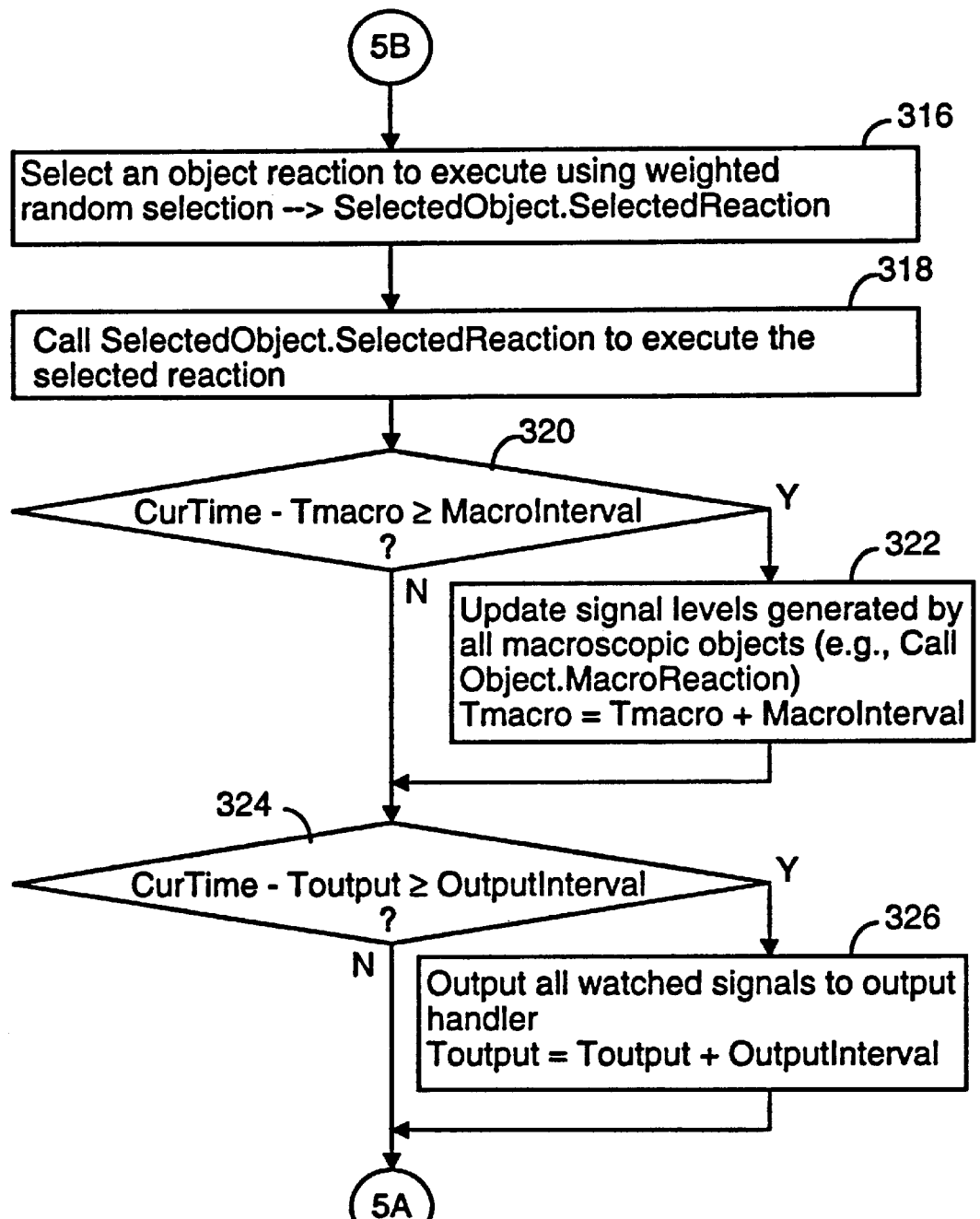

Referring to FIG. 5 and the pseudocode procedures in Tables 1–5, the simulation procedure first initializes itself (300) by:

receiving a list of objects representing the biochemical network to be simulated;

defining initial signal levels for all signals in the defined biochemical network;

defining other initial object values;

setting the "changed flags" for all objects, to force the computation of reaction probabilities for all objects when the main loop of the simulation procedure is first executed (see discussion of step 310, below);

defining initial object dependencies, indicating which objects have reactions whose probability of occurrence depends on a signal generated by another object;

defining a list of watched signals whose values are to be output by the simulator;

defining an update interval, Toutput, for updating the values of the watched signals that are sent to an output data handler;

defining an update interval, Tmacro, for updating the signals output by macroscopic objects; and defining a simulation period, including a start time (StartTime) and an end time (EndTime), and initializing the current simulation time (CurTime) to be equal to the start time.

At the beginning of the main simulation loop, the current simulation time is compared with the simulation end time (302), and the simulation is completed with a call to the output procedure (304) if the current simulation time is equal to or greater than the simulation end time. Otherwise (302, N), execution of the main simulation loop is enabled.

An initial step (306) of the main simulation loop in the preferred embodiment is to call the "Mark" procedure (190*a*, FIG. 3) for all objects to determine, for each object, whether the object is to be handled as a mesoscopic object or a macroscopic object. For purposes of this discussion, a mesoscopic object is one that exhibits stochastic behavior at a level that the user is interested in simulating, while a macroscopic object is one that generates a signal that exhibits a relatively steady rate of change over time and therefore does not exhibit stochastic behavior. For some signals, a threshold is defined, such as 100 molecules per cell, at which stochastic behavior becomes irrelevant and above which the object's behavior is simulated using a simpler, less computationally intensive procedure (i.e., the corresponding object's macroscopic reaction procedure) than the reaction procedure used when the signal level is below the threshold. The meso/macro threshold can be defined differently for different object classes, and the corresponding determination is made by the Object.Mark procedure for each object. For some signals, the corresponding object reaction procedure is always defined as mesoscopic or always defined as macroscopic, in which case the Mark procedure for the corresponding object class simply returns a constant value.

Next, some objects have multiple internal states that require selection prior to selecting an object reaction to simulate. The StateUpdate method of each object is called (308) to perform this function. For objects having a single internal state, the StateUpdate method simply stores a constant value in the state field 192 of the object's data array. For objects having multiple internal states, the selection of an internal state depends on the biochemistry of the corresponding biochemical element. For instance, some promoters have multiple sites for receiving specific molecules, and the state of such promoters depends on the current occupancy of those sites. Furthermore, in most cases the promoter object's internal states can be assigned relative probabilities based on measurements of binding energies associated with the various object states. For example, for multisite promoters, the probability of each possible internal state is defined as:

$$P(S) = \frac{e^{\frac{-\Delta G_S}{RT}} [E_1]\ldots[E_m]}{\sum_s e^{\frac{-\Delta G_S}{RT}} [E_1]\ldots[E_m]}$$

where S represents the state of promoter, $\Delta G_S$ is the binding energy for a given state S, $E_i$ is the signal level (i.e., concentration level) of the protein occupying the ith site of the promoter site. Note that the protein occupying a site may be different for different states, and that the $[E_i]$ factors are multiplied with each other. Thus, if N sites are occupied by the same protein, then a factor of $[E_i]^N$ would be used in the probability formula. Further, since the denominator of the P(S) formula is the sum of the probabilities for all states, the state probability values are normalized and add up to a total of "1".

The relative probability values for an object's internal states are recomputed by the StateUpdate procedure only if at least one of the objects on which the internal state probability values depend has been changed since the last time the internal state probability values were computed. This is determined by inspecting the changed flag 177 value for all the objects in the object dependency list 178 for the object whose internal state needs to be determined.

Given a set of relative probability values, the StateUpdate method for the object generates a random number and then uses that number to select a corresponding object state. More specifically, given the random number, the probabilities of the states are summed in a fixed sequential order until the sum is greater than the random number, and the state associated with the probability value that caused the sum to exceed the random number is selected as the selected state. For instance, if the relative probability of four states for an object were all 0.25, and the generated random number value was 0.41, then the second internal state value would be the one selected.

After selecting internal states for all objects (308), the simulator next recomputes the probabilities for each mesoscopic object if the probability of any reaction by the object depends on another object whose changed flag is set (310). The objects whose reaction probabilities need recomputing are determined by inspecting the changed flag 177 value for all the objects in the object dependency list 178 for the object whose internal state needs to be determined. If an object's probabilities need recomputation because it depends on a changed object, then the all reaction probabilities for the object are recomputed by calling the object's Query method. Note that the reaction probabilities may be a function of the object's internal state, selected by the previous step (306). The reaction probabilities computed by the Query method are stored in the Reaction Queue 196 of each object. Each such reaction probability is expressed in terms of the expected number of reactions per second for the respective reaction. For example, a reaction whose average reaction rate is once per 10 seconds would have a reaction probability of 0.1. The reaction probabilities computed by step 310 are completely distinct from the internal state relative probabilities discussed above with respect to step 308.

Reaction probabilities that do not depend on any changed objects are not recomputed by step 310.

After all reaction probabilities requiring recomputation have been recomputed, the changed flags of all objects are cleared (312). The use of the changed flag 177 and the dependency lists 178 helps to reduce the amount of computational resources used to determine reaction probabilities.

Next (314), the reaction probabilities for all reactions of all mesoscopic objects are summed to generate a total, instantaneous reaction probability value, TP. TP represents the average number of expected reactions of all types per second, at that time. Note that the expected number of reactions per second is highly variable, depending on the overall instaneous state of the network being simulated.

From the value of TP, an inverse Poisson function is used in conjunction with a random number generator to select the amount of time $\Delta RT$ until the next reaction time, and to update the current simulation time CurTime to the next reaction time. For instance, if TP is equal to 2.5, representing 2.5 reactions per second, then the mean of the Poisson distribution for $\Delta RT$ will equal 0.4 seconds, but its sampled value may be any value from very close to 0 to values of 5 seconds and more.

Chemical reactions in the cell can be characterized as stochastic events following a Poisson distribution in time and space with exponentially distributed time intervals between successive reaction events. That is, the probability density for the next reaction at time t is equal to (1/Tmean) $e^{t/Tmean}$ where Tmean is the instantaneous average time parameter of the exponential distribution. The variance of the exponential distribution is $(Tmean)^2$ and the distribution is highly skewed about the mean. For example, sixty-nine percent of the intervals will be shorter than the average, but about 1 in 20 will be greater than 3 times the average interval.

After a next reaction time has been selected, a next object reaction to execute is selected using a weighted random selection function. In particular, the weighted random selection function generates a random number and scales the generated random number in accordance with the instantaneous total reaction probability value, TP, to generate a scaled random number. Given the scaled random number, the probabilities of the reactions are summed in a fixed sequential order (e.g., in the order that objects are listed in the object list 120 and that reactions are listed within the object data arrays 186) until the sum is greater than the scaled random number, and the object reaction associated with the probability value that caused the sum to exceed the scaled random number is selected as the selected object reaction.

Then, the selected object reaction is executed (i.e., performance of the reaction is simulated) by calling the associated method, SelectedObject.SelectedReaction (318). The changed flag of the object whose reaction was executed is set if execution of the reaction method causes any parameter or output signal of the object that is visible to other objects to have changed in value. In addition, if the execution of the selected object reaction method causes one or more new objects to be added to the simulation, or causes the deletion of an object from the simulation, the object dependencies 178 stored in the object list 120 are updated accordingly.

At this point, one stochastic reaction has been performed. Before executing the next loop of the main simulator procedure, the procedure checks to see if it is time to update the macroscopic objects (320), and also checks to see if it is time to send a new vector of output values to the output handler (324). In particular, if the difference between the current simulation time (CurTime) and the last macroscopic time update (Tmacro) is greater than the macroscopic update interval (320)

$$CurTime-Tmacro \geq MacroInterval$$

then the signal levels of all macroscopic objects are updated by calling their respective MacroReaction methods, Object-.MacroReaction (322). Furthermore, if the difference between the current simulation time and the last output update time (Toutput) is greater than the output update interval (324)

$$CurTime-Toutput \geq Output\ Interval$$

then the signal levels of all watched output signals are passed to the output handler procedure (326).

Finally, the main simulation loop resumes execution at step 302.

By repeated execution of the simulation loop, operation of all the stochastic processes, as well as all the macroscopic processes associated with the objects in the biochemical network is simulated over a period of time, and the resulting signals produce interactions between the objects in the biochemical network that cause the simulated network to function.

The present invention is equally applicable to simulation of biochemical networks found in, or hypothetically suitable for use in, both prokaryotic cells and eukaryotic cells.

Examples of Object Methods

1. RNAP Object Methods

Referring to Table 2, the model for RNAP in the preferred embodiment is a RNAP object class having several methods, including a StateUpdate method, a Query method and a few Reaction methods. Each RNAP object corresponds to a RNAP molecule on a DNA strand.

The RNAP.StateUpdate method (called at the beginning of each simulation loop) determines whether a RNAP molecule is blocked by another RNAP molecule from moving one position down the DNA strand on which it is located. Each RNAP object is linked to the next RNAP molecule ahead of it, if any. If a RNAP molecule is blocked, its state is set to "Blocked." Otherwise its state is set to "Unblocked."

The RNAP.Query method sets the probability values for three potential RNAP reactions: 1) a RNAP movement reaction, 2) a RNAP antitermination reaction, and 3) a RNAP antitermination reaction. All three reaction probabilities are set to zero if the RNAP object's state is "Blocked," meaning that the simulated RNAP molecule has zero probability of moving at the current time. Otherwise, if the RNAP object's position does not coincide with a terminator or antiterminator, its RNAP movement reaction probability is set to a fixed, predefined value used for all unblocked RNAP molecules.

If the RNAP object's position coincides with an antiterminator site, the probability of the RNAP antitermination reaction is computed based on the instantaneous concentrations of the antitermination proteins associated with that antitermination site, and the probability of the RNAP movement reaction (without antiterminating the RNAP object) is also computed based on the instantaneous concentrations of the antitermination proteins. Thus, when the RNAP object's position coincides with an antiterminator site the RNAP movement reaction and the RNAP antitermination reaction will be assigned non-zero values.

If the RNAP object's position coincides with a terminator site, the probability of the RNAP termination reaction is given a fixed, high value if the RNAP object has not been antiterminated and is given a fixed, lower value if the RNAP object has been antiterminated. Similarly, the probability of the RNAP movement reaction is given a fixed, low value if the RNAP object has not been antiterminated and is given a fixed, higher value if the RNAP object has been antiterminated. These reaction probability values are fixed for each terminator she and are parameters specified for each terminator object.

The RNAP.Reaction1 method, which is called if a RNAP molecule is selected to "execute a RNAP movement reaction," simply increases the RNAP object's position by one "step", which in the preferred embodiment corresponds to one or more nucleotides. In addition, the ChangedFlag for the RNAP object is set.

If the resulting RNAP object position coincides with the position of a Gene on the DNA strand special processing is performed. The RNAP.Reaction1 method creates a new Transcript object when the RNAP molecule's position coincides with the gene's "starting site," which is simply a predefined position on the DNA strand. The new transcript object is linked to the RNAP object for later reference. After the RNAP molecule passes a gene's starting site, each additional movement of the RNAP molecule position causes the length of the corresponding Transcript object to be increased, until the RNAP molecule progresses past the end of the gene.

The RNAP.Reaction2 method antiterminates a RNAP object simply by setting the Object.AntiterminationStatus parameter (stored in part of the State field 192) for the RNAP object to a value of "Yes". In addition, the ChangedFlag for the RNAP object is set.

The RNAP.Reaction3 method terminates a RNAP object by deleting the RNAP object from the simulation.

As indicated above, the methods for the RNAP object class could also include a user selectable, simpler model, for instance a model in which RNAP molecule movement blocking is ignored. For instance, in such a model the RNAP object could be set up to move to a next DNA strand position at a calculated future time. In this model, the internal state of the RNAP object would be set to "asleep" and its reaction probability would be set to zero until the simulation time reaches the calculated future time, at which point the internal state of the RNAP object would be set to "ready_to_move" and its reaction probability would be set to a very high value. Upon execution of the RNAP movement reaction, the process of calculating a future movement time and changing to an internal "asleep" state would be repeated. In this way RNAP reactions would be removed from the reaction queue of the simulator most of the time, thereby reducing the computational resources used for simulating the operation of individual RNAP complexes.

2. Ribosome Initiation Method of the Transcript Object

Referring to Table 3, the ribosome initiation method models two competitive reactions: one for RNase binding to the transcript, leading to inactivation (RNase binding reaction), and one for initiation of a Ribosome object (Ribosome initiation reaction) leading to production of a protein. The Transcript object's Query method sets up the probability for the two reactions. In particular, if the Transcript object's "RNase" state is not equal to "consumed," then the two possible reactions are given their standard, predefined reaction probabilities. In the preferred embodiment, the reaction probabilities are set up so that the ratio of the probability of the Ribosome initiation reaction to the probability of the RNase binding reaction equals the mean number of proteins expected to be generated per transcript. If the transcript object's RNase state is equal to "consumed," then both possible reaction types are given a probability of zero.

When the RNase binding reaction is executed for a transcript object, the state of the object is changed to "consumed," which then prevents the transcript object from "acquiring" additional ribosome objects. When the "ribosome" reaction is executed for a transcript object, a new Ribosome object is created and linked to the Transcript object.

3. Ribosome Object Methods

Referring to Table 4, the Ribosome object is similar to the RNAP object in that its main action is to move down a strand, in this case that of a mRNA transcript, except when its movement is blocked by another ribosome molecule positioned ahead of it. Further, when a ribosome's position coincides with a "stop code" position on the transcript, a new protein molecule is released, corresponding to the protein coded by the gene that is being transcribed by a corresponding RNAP molecule.

The Ribosome.StateUpdate method (called at the beginning of each simulation loop) determines whether a Ribosome molecule is blocked by another Ribosome molecule from moving one position down the transcript on which it is located. Each Ribosome object is linked to the next Ribosome molecule ahead of it, if any. If a Ribosome molecule is blocked by another Ribosome molecule positioned immediately ahead of it, its state is set to "Blocked." Otherwise its state is set to "Unblocked."

The Ribosome.Query method sets the Ribosome molecule's "reaction" probability to zero if its state is "Blocked," meaning that the Ribosome molecule has zero probability of moving at the current time, otherwise sets its reaction probability to a fixed, predefined value used for all unblocked Ribosome molecules.

The Ribosome.Reaction method, which is called if a Ribosome molecule is selected to "execute a reaction," simply increases the Ribosome object's position by one "step". In addition, the changed flag for the Ribosome object is set. If the resulting Ribosome object position coincides with the "stop code" position of the transcript on which it is located, the protein molecule count for the corresponding Gene object is increased by one, indicating that a protein molecule has been created and released, and then the Ribosome object is deleted from the simulation since its work is completed.

4. Promoter Object Methods

Referring to Table 5, the model for promoters in the preferred embodiment is a promoter object class having several methods, including a StateUpdate method, a Query method and a Reaction method. Each promoter object corresponds to a promoter site on a DNA strand.

The Promoter.StateUpdate method (called at the beginning of each simulation loop) determines which of several possible internal states is to be associated with the promoter site for a particular simulation loop. If any of the objects on which the internal state probabilities depend has a set changed flag, all the promoter state probabilities are recomputed. Then a random number X is generated and one of the possible internal states is selected based on that random number, as is described in more detail above.

The Promoter.Query method sets the promoter's reaction probability based on the selected internal state. If any of the objects on which the reaction probability depends has a set changed flag, the promoter reaction probability is recomputed.

The Promoter.Reaction method, which is called if a Promoter object is selected to "execute a reaction," generates a new RNAP object, links the new RNAP object to the promoter object, links the previously generated RNAP object (if any) to the new RNAP object, sets the new RNAP object's position on the associated DNA strand, and sets the ChangedFlag for the new RNAP object.

Monte Carlo Procedure

Since each simulation is the product of many stochastic reactions, the results generated by one simulation run are only one sample of the behavior of a cell or organism having the specified biochemical network. To characterize the likely behavior of a group of such cells or organisms, a Monte Carlo procedure is used to re-execute the simulation N times, (e.g., 20 times) and to then generate charts showing the signal paths of "average" cells as well as the signal paths X standard deviations (e.g., 1 standard deviation) above and below the average.

Figure 6A:
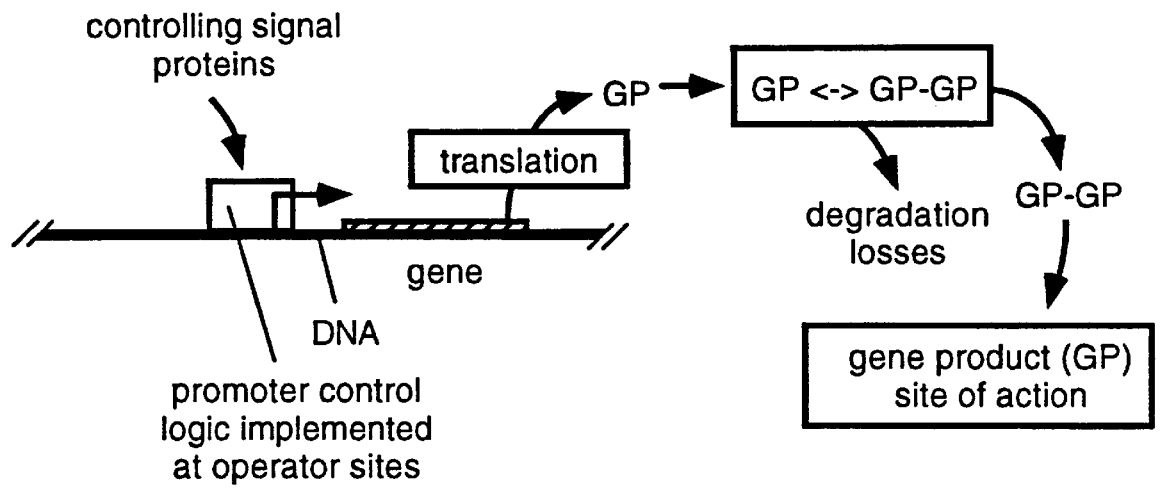
FIG. 6A and FIG. 6B are schematic diagrams representing simple biochemical networks.

In genetic regulatory networks information is frequently transmitted from point to point by changing chemical concentrations. FIG. 6A shows a common structure for an information link based on control of protein production. The rate of transcript initiation can be a complex function of the concentration of controlling chemical species. In the case shown the active form of the signal is assumed to be a dimer. When the input signal concentrationa produce a high rate of transcript initiation, protein production increases, in effect broadcasting the information that the promoter is "on". The message is "received" or detected by the concentration-dependent response at the proteins signal's site(s) of action, which often is one or several promoter sites, stimulating an appropriate response. The instantaneous level of any chemical signal is determined by the cumulative balance between production and loss mechanisms. Using signaling links constructed with this and other mechanisms, interlocking networks of great complexity are created that create, respond to, and propagate cellular control signals. These networks simulate the biochemical logic that controls actual or hypothetical cells.

Figure 6B:
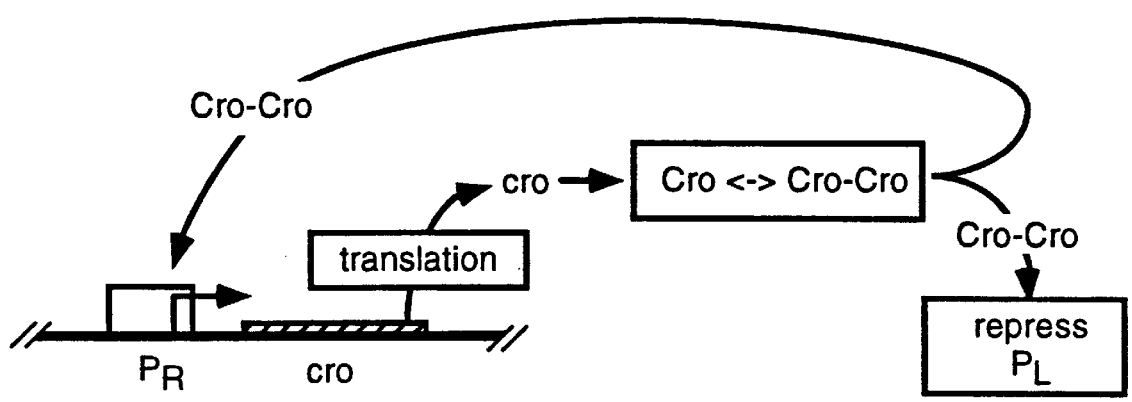

FIG. 6B shows an example of a common, simple link configuration, the configuration that produces Cro dimers from PR-initiated transcripts in the Lambda phage genetic network. Promoter PR is autoregulated by the Cro dimer.

Figure 7A:
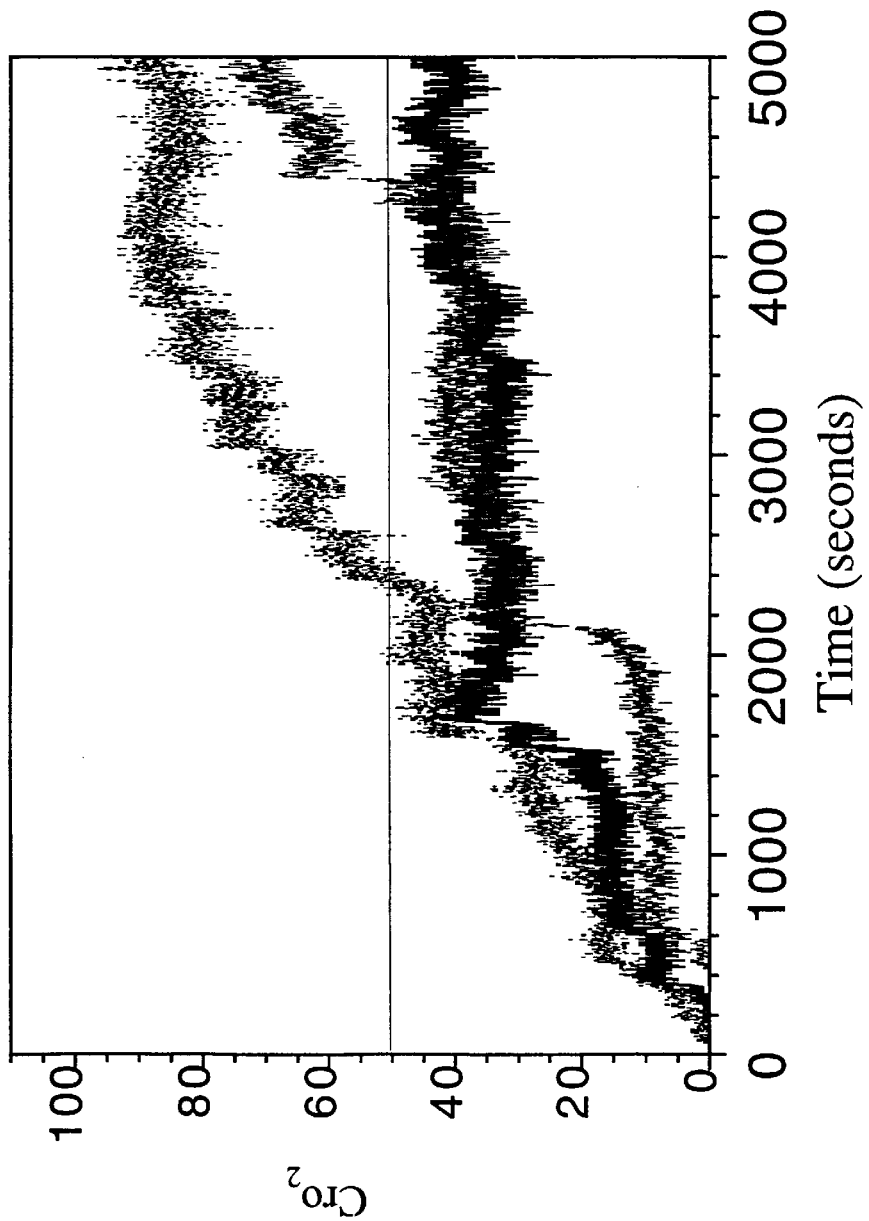
FIGS. 7A and 7B are graphs representing simulation results generated by repeated simulations of the network shown in FIG. 6B using the Monte Carlo procedure of the preferred embodiment.

FIG. 7A shows the pattern of Cro dimer signal growth due to production from promoter PR at multiplicity of infection (MOI) of 1 (one PR promoter controlling one cro) for three stochastic simulation runs of the network shown in FIG. 6B. The diversity between the three runs results from differences in the chance events in all the stochastic mechanisms in the circuit (transcript initiation, protein production, protein degradation). The abrupt jumps in dimer concentration result from random occurrence of high protein outputs from a transcript. The intervals of flat or declining signal result from chance occurrence of some combination of long transcript intervals and low protein outputs per transcript produced.

Figure 7B:
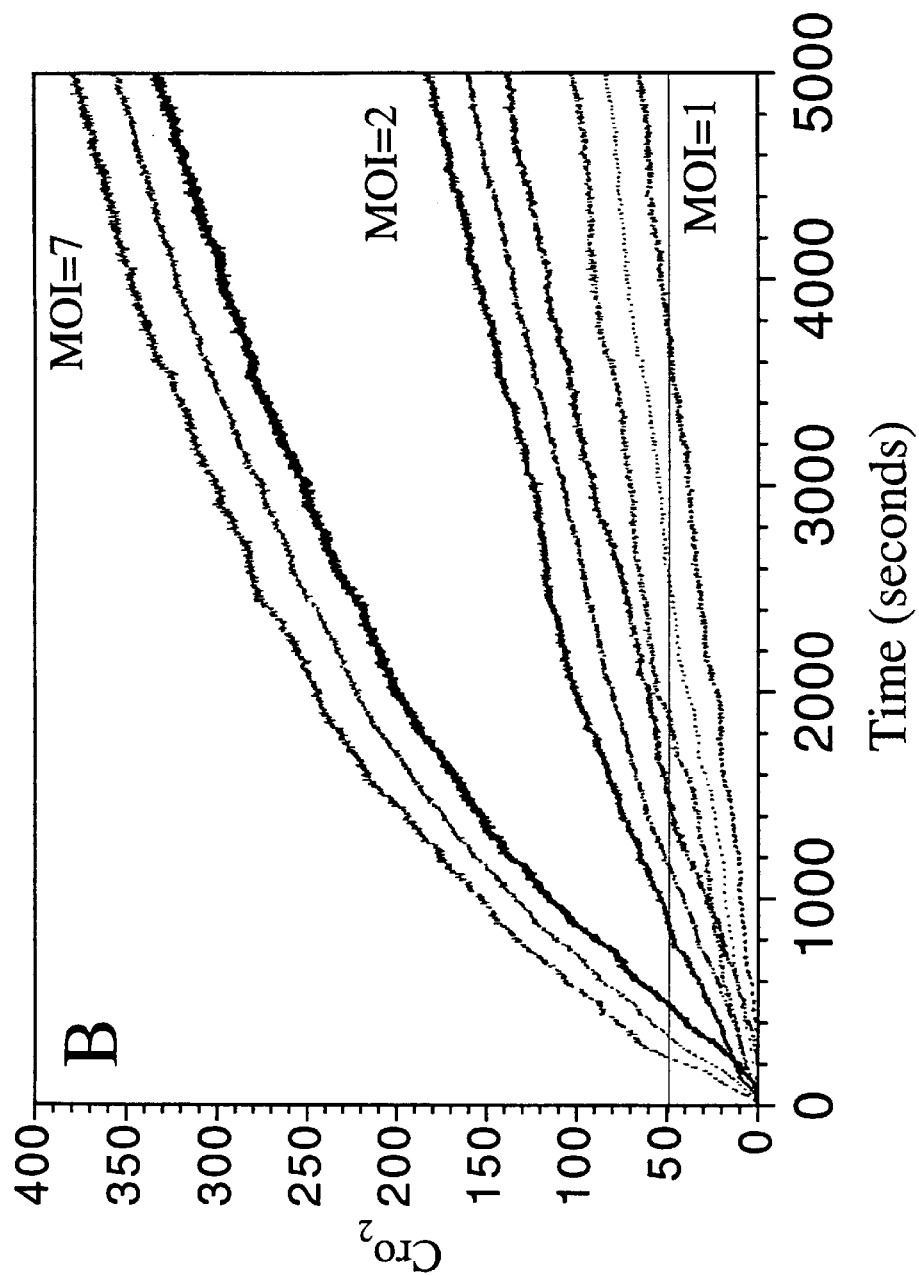

FIG. 7B shows the mean and standard deviation of the Cro dimer signal for MOI equal to 1, 2, and 7 (calculated from 20 simulation runs at each MOI of the network shown in FIG. 6B). The horizontal line at 50 dimers represents a levels of effectivity at the Cro dimer signal's site of action. Higher gene dosage (MOI) produces proportionately quicker time to effectivity and proportionately lower uncertainty in that time. The ±1 sigma range of time to effectivity differs by approximately a factor of two for all these cases.

As shown, the time pattern of protein production is strongly stochastic. These stochastic fluctuations are one cause of the divergent genetic circuit outcomes observable as random macroscopic differences in cell phenotypes. Cells can exploit these inherent fluctuations to achieve non-genetic diversity where this makes the population more capable of surviving in a wide range of environments. In other regulatory circuits, fluctuations in signal concentration may represent a driving selection factor in evolution of circuit design and of reaction-determining parameters to favor predictable and stable outcomes. The auto-regulatory feedback loops that are pervasive elements of bacterial regulatory subcircuits can be important contributors to the predictable and stable outcomes.

Genetic regulatory circuit simulations require stochastic reaction event-level modeling and Monte Carlo techniques because the concentration of intracellular species is frequently so low that the assumptions underlying kinetic equations are not met. Also, the fluctuation level in regulatory protein concentrations is itself of significance and must be estimated. Fluctuation parameters can only be estimated with a stochastic simulation algorithm. When investigating the detailed functioning of genetic regulation, experimental techniques that measure the time evolution of average concentrations over a cell population can mask important interactions. Techniques that monitor chemical events in individual cells are needed to monitor genetic circuit dynamics.

Alternate Embodiments

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

For instance, future embodiments of the present invention will likely include alternate models or object classes for simulation of:

RNAP and ribosome movement along DNA and mRNA, respectively;

transcription control;

chromosome replication;

DNA modification reactions (e.g., deletion or insertion of DNA segments, such as the excision of an integrated prophage from the lambda phage network);

eukaryotic organelles such as mitochondria;

transport across the eukaryotic nuclear membrane; and membrane bound sensors and other elements of two component systems.

Future embodiments of the present invention will likely also include alternate computer architectures, such as multiple CPU architectures allowing for distributed computation of object methods.

TABLE 1

Pseudocode Representation of Biochemical Simulator Procedure

Procedure: Simulate (ObjectList)
{
Receive list of objects (ObjectList) representing the Biochemical Network to be simulated
Define initial signal levels
Define other initial object values (e.g., RNAP positions, if any, on DNA
    sequences)
Set "changed flag" for all signals
Define initial object dependencies
Define signals to be monitored (output signals)
Define update interval, TOutput, for output signals
Define update interval, TMacro, for macroscopic objects
Define simulation period: StartTime, EndTime
CurTime = StartTime      /*   Beginning of Simulation Time */
Do Until CurTime ≧ EndTime      /*   End of Simulation Time */
    {
    Call Mark method of all objects to update whether the object is currently a
        mesoscopic or macroscopic object.
    For all Objects that have internal states {
        /*   This includes Instantaneous Update objects, such as Promoters,
            Boolean Gates, etc. */
        /*   The following steps are performed by calling "Object.StateUpdate"*/
        For each internal state that depends on another signal that has been
            updated {
            Update the signal's state probabilities
            }
        If Object's state variable is Stochastic {
            Select a state using weighted random number selection
            }
        If Object's state variable is Deterministic {
            Select a state using its state update method
            }

TABLE 1-continued

Pseudocode Representation of Biochemical Simulator Procedure

```
        }
    For all Mesoscopic objects
        {
        If any of the Object's reactions have a probability that depends on
                another object. (i.e., signal) that has been updated {
            Call Object.Query       /* Recomputes reaction probabilities */
                }
        /*  Object includes Reaction Queue with all candidate reactions for that
            object, and their probabilities */
        }
    Clear the "changed flag" for all objects
    Use Poisson Process Function (ObjectList) to select (i.e., calculate) next
            reaction time (ΔRT)
            CurTime = CurTime + ΔRT
    Select an object reaction to execute using weighted random selection
            -> SelectedObject
    /*  Simulate the selected object reaction and mark as changed all signals
            whose values are changed by the simulated object reaction */
    Call SelectedObject.Reaction
    If the executed object reaction created or deleted any objects {
            Update object dependencies }
    If (CurTime - TMacro) ≧ MacroInterval {
        Update signals Levels generated by all macroscopic objects
        TMacro = TMacro + MacroInterval
        }
    If (CurTime - TOutput) ≧ OutputInterval {
        Output all watched signals levels to output handler
        TOutput = TOutput + OutputInterval
        }
    }   /*  End of Simulation Loop */
Call Output Procedure to process output data
}   /*  EndofProcedure */
```

TABLE 2

Pseudocode Representation of RNAP Object Methods

```
Procedure RNAP.StateUpdate
{
/* Determine if RNAP is blocked from moving by another RNAP    */
AheadObject = next object, if any, ahead of ThisObject on same DNA strand
If AheadObject.Position = ThisObject.Position + 1 + RNAPfootprint {
        ThisObject.State Blocked
        }
Else    {
        ThisObject.State = Unblocked
        }
Return
}
Procedure RNAP.Query
{
If ThisObject.State = Blocked
        ThisObject.Reaction1.Probability = 0        /* RNAP Propagation    */
        ThisObject.Reaction2.Probability = 0        /* RNAP Antitermination */
        ThisObject.Reaction3.Probability = 0        /* RNAP Termination    */
        }
Else    {
        /* Standard Reaction Probabilities for Unblocked RNAP: */
        ThisObject.Reaction1.Probability = NormalProbabilityOfPropagation
        ThisObject.Reaction2.Probability = 0        /* RNAP Antitermination /*
        ThisObject.Reaction3.Probability = 0        /* RNAP Termination /*
        If ThisObject.Position coincides with the position of an Antiterminator    {
            If ThisObject.AntiterminationStatus = No    {
                ProbabilityOfAtermEscape = Function1(concentration of
                    antitermination proteins at this time)
                ProbabilityOfAntitermination = Function2(concentration of
                    antitermination proteins at this time)
                ThisObject.Reaction1.Probability = ProbabilityOfAtermEscape
                ThisObject.Reaction2.Probability = ProbabilityOfAntitermination
                ThisObject.Reaction3.Probability = 0
                {
            {
        If ThisObject.Position coincides with the position of a Terminator    {
            If ThisObject.AntiterminationStatus = Yes    {
```

TABLE 2-continued

Pseudocode Representation of RNAP Object Methods

```
                ThisObject.Reaction1.Probability = HighProbabilityOfTermEscape
                ThisObject.Reaction2.Probability = 0
                ThisObject.Reaction3.Probability = LowProbabilityOfTermination
                }
        Else {
                ThisObject.Reaction1.Probability = LowProbabilityOfTermEscape
                ThisObject.Reaction2.Probabilit = 0
                ThisObject.Reaction3. Probability = HighProbabilityOfTermination
                }
        }
    }
Return
}
Procedure RNAP.Reaction1    /* Propagate RNAP */
{
ThisObject.Position = ThisObject.Position+1
Mark ChangedFlag for ThisObject
If ThisObject.Position coincides with the position of a Gene {
        /* Create and Lengthen Transcript Objects as RNAP moves over a Gene */
        If ThisObject.Position = Gene.StartingSite {
    Create new Transcript Object and link it to ThisObject
    }
    Else   {
        if Action MoveOnePosition   {
                Increment Length of linked Transcript Object
                }
        }
    }
Return
}
Procedure RNAP.Reaction2   /*   Antiterminate RNAP   */
{
/* Special Processing for Antiterminator after sites */
ThisObject.AntiterminationStatus = Yes
Mark ChangedFlag for ThisObject
Return
{
Procedure RNAP.Reaction3   /*   Terminate RNAP   */
{
/* Attenuate RNAP molecules that are not antiterminated */
Delete ThisObject (RNAP object) from simulation
Return
}
```

TABLE 3

Pseudocode Representation of Transcript Object Methods

```
Procedure Transcript.Reaction1
{
/*   RNase and Ribosomes compete for use of Binding Site on the Linked
    Transcript Object   */
ThisObject.RNaseState = Consumed
Return
}
Procedure Transcipt.Reaction2
{
Create Ribosome Object and link it to the Transcript Object
Return
}
Procedure Transcript.Query
{
If ThisObject.Position ≧ Gene.BindingSite
    and ThisObject.RNaseState ≠ Consumed
        {
        ThisObject.Reaction1.Probability = ThisObject.RNaseProbability
        ThisObject.Reaction2.Probability = ThisObject.RibosomeProbability
        }
Else
        {
        ThisObject.Reaction1.Probability = 0
        ThisObject.Reaction2.Probability = 0
        If there are no more Ribosomes on this transcript {
```

TABLE 3-continued

Pseudocode Representation of Transcript Object Methods

```
        Delete ThisObject }
        }
Return
{
```

TABLE 4

Pseudocode Representation of Ribosome Object Methods

```
Procedure Ribosome.StateUpdate
{
/* Determine if Ribosome is blocked from moving by another Ribosome
*/
AheadObject = next object, if any, ahead of ThisObject on same transcript
If AheadObject.Position = ThisObject.Position + 1 RibosomeFootprint
    {
    ThisObject.State = Blocked
    }
Else {
    ThisObject.State = Unblocked
    }
Return
}
```

TABLE 4-continued

Pseudocode Representation of Ribosome Object Methods

```
Procedure Ribosome.Query
{
If Object.State = Blocked {
    ThisObject.Reaction.Probability = 0
    }
Else {
    ThisObject.Reaction.Probability = Ribosome.Reaction.Probability
    }
Return
}
Procedure Ribosome.Reaction
{
ThisObject.Position = ThisObject.Position+1
Mark ChangedFlag for ThisObject.Position
/* Generate Protein if Coding Frame has been reached */
If ThisObject.Position = Transcript.StopCodePosition {
    GeneObject = GeneObject associated with the Transcript Object
    GeneObject.Signal = GeneObject.Signal + 1
    Mark Changed Flag for GeneObject.Signal
    Delete ThisObject /* Ribosome molecule's job is completed */
    }
Return
}
```

TABLE 5

Pseudocode Representation of Promoter Object Methods

```
Procedure Promoter.StateUpdate
{
/* Determine Promoter State */
If any of the objects on which the promoter state depends have a set
changed flag {
    Recompute Promoter State Probabilities
    }
/* Select a state based on a generated random number */
X = RandomNumber()
ThisObject.State = SelectState(ThisObject, X)
Return
}
Procedure Promoter.Query
{
If any of the objects on which the promoter reaction probability depends
have a set changed flag {
    Recompute probability of promoter adding a RNAP to DNA strand
    }
ThisObject.Reaction.Probability = computed probability
Return
}
Procedure Promoter.Reaction
{
Generate RNAP object
Mark ChangedFlag for new RNAP Object
RNAPObject.Position = Promoter.Position + 1
    /* this blocks new RNAP objects from being generated until the
    just created RNAP object moves at least one position down the
    DNA strand */
Link new RNAP object to this Promoter
Link the last generated RNAP object (if any) to the new RNAP object
    /* new RNAP object must be able to determine if its progress is
    blocked by the next RNAP object (if any) ahead of it on the
    DNA strand. */
Return
}
```

What is claimed is:

1. A method of simulating the operation of a biochemical network, said method comprising the steps of:

(A) receiving and storing in a computer memory a list of objects, each object representing a biochemical mechanism in said biochemical network;

(B) for each of at least a subset of said objects, associating one or more signals with said each object; a first subset of said signals representing quantities or concentrations of associated proteins; designating a second subset of said signals as output signals;

(C) associating a set of methods with each object in said list of objects; for each of at least a subset of said objects, said associated methods including one or more probability determination methods for determining one or more reaction probabilities for one or more biochemical reactions associated with said object, and one or more reaction simulation methods for simulating performance of one or more associated biochemical reactions;

(D) for a specified simulation time period, simulating operation of said biochemical network, including executing at least a subset of said probability determination methods to determine reaction probabilities for at least a subset of said biochemical reactions associated with said objects, selecting ones of said reaction simulation methods to execute in accordance with said determined reaction probabilities, and executing said selected ones of said reaction simulation methods; wherein execution of said selected ones of said reaction simulation methods causes associated ones of said signals to be updated;

(E) generating output data representing signal values of at least a subset of said output signals during said specified simulation time period.

2. The method of claim 1, wherein a subset of said objects in said list comprise RNAP objects that represent RNAP complexes that bind to and move along respective DNA strands represented by other ones of said objects;

a third subset of said signals comprising RNAP position signals representing physical positions of said RNAP complexes on said respective DNA strands; and said simulating step including determining movement reaction probabilities for each RNAP object in said list that represents a RNAP complex bound to a respective DNA strand, selecting when to simulate movement of said RNAP complexes represented by said RNAP objects in accordance with said movement reaction probabilities, and simulating movement of said RNAP complexes represented by said RNAP objects by updating said RNAP position signals.

3. The method of claim 1, wherein a subset of said objects in said list comprise objects representing stochastic reaction mechanisms;

said simulating step including determining reaction probabilities for said objects representing stochastic reaction mechanisms; selecting in a stochastic manner, based on said reaction probabilities, simulation times at which to simulate performance of stochastic reactions associated with said stochastic reaction mechanisms, and simulating performance of said stochastic reactions at said selected simulation times;

said simulating step including updating signals associated with said objects representing stochastic reaction mechanisms, and recomputing said reaction probabilities for said objects representing stochastic reaction mechanisms based on said updated signals.

4. The method of claim 3, wherein a subset of said objects in said list comprise objects representing continuous, macroscopic reactions; and said simulating step including simulating said continuous, macroscopic reactions, thereby updating signals associated with said objects representing said continuous, macroscopic reactions.

5. A method of simulating the operation of a biochemical network, said method comprising the steps of:
   (A) receiving and storing in a computer memory a set of objects, each object representing a biochemical reaction or mechanism in said biochemical network;
   (B) for each of at least a subset of said objects, associating one or more signals with said each object; a first subset of said signals representing quantities or concentrations of associated proteins; designating a second subset of said signals as output signals;
   (C) for a specified simulation time period, simulating operation of said biochemical network, including (C1) determining reaction probabilities for at least a subset of said biochemical reactions associated with said objects, (C2) selecting ones of said biochemical reactions to simulate in accordance with said determined reaction probabilities, (C3) simulating performance of said selected ones of said biochemical reactions, wherein simulating performance of said selected ones of said biochemical reactions causes associated ones of said signals to be updated, and (C4) redetermining said reaction probabilities in accordance with said updated signals; and
   (D) generating output data representing signal values of at least a subset of said output signals during said specified simulation time period.

6. The method of claim 5,
   wherein a subset of said objects comprises RNAP objects that represent RNAP complexes that bind to and move along respective DNA strands represented by other ones of said objects;
   a third subset of said signals comprising RNAP position signals representing physical positions of said RNAP complexes on said respective DNA strands; and
   said simulating step including determining movement reaction probabilities for each said RNAP object that represents a RNAP complex bound to a respective DNA strand, selecting when to simulate movement of said RNAP complexes represented by said RNAP objects in accordance with said movement reaction probabilities, and simulating movement of said RNAP complexes represented by said RNAP objects by updating said RNAP position signals.

7. The method of claim 5,
   wherein a subset of said objects comprise objects representing stochastic reaction mechanisms;
   said simulating step including determining reaction probabilities for said objects representing stochastic reaction mechanisms; selecting in a stochastic manner, based on said reaction probabilities, simulation times at which to simulate performance of stochastic reactions associated with said stochastic reaction mechanisms, and simulating performance of said stochastic reactions at said selected simulation times;
   said simulating step including updating signals associated with said objects representing stochastic reaction mechanisms, and recomputing said reaction probabilities for said objects representing stochastic reaction mechanisms based on said updated signals.

8. The method of claim 7,
   wherein a subset of said objects comprise objects representing continuous, macroscopic reactions; and
   said simulating step including simulating said continuous, macroscopic reactions, thereby updating signals associated with said objects representing said continuous, macroscopic reactions.

9. A biochemical network simulator for simulating the operation of a biochemical network having a multiplicity of biochemical mechanisms, comprising:
   a central processing unit;
   a computer memory, coupled to said central processing unit, for storing data representing said biochemical mechanisms in said genetic network, said stored data including a set of objects, each object representing a biochemical mechanism in said biochemical network;
   said stored data including, for each of at least a subset of said objects, one or more signals associated with said each object; a first subset of said signals representing quantities or concentrations of associated proteins; said stored data further including output signal designations designating a second subset of said signals as output signals;
   said computer memory further storing a set of methods associated with each object in said set of objects; for each of at least a subset of said objects, said associated methods including one or more probability determination methods for determining one or more reaction probabilities for one or more biochemical reactions associated with said object, and one or more reaction simulation methods for simulating performance of one or more associated biochemical reactions;
   a simulation procedure, executed by said central processing unit, that simulates operation of said biochemical network by executing at least a subset of said probability determination methods to determine reaction probabilities for at a subset of said biochemical reactions associated with said objects, selecting ones of said reaction simulation methods to execute in accordance with said determined reaction probabilities, and executing said selected ones of said reaction simulation methods; wherein execution of said selected ones of said reaction simulation methods causes associated ones of said signals to be updated; and
   an output procedure, executed by said central processing unit, for generating output data representing signal values for ones of said output signals.

10. The biochemical network simulator of claim 9,
    wherein a subset of said objects comprise RNAP objects that represent RNAP complexes that bind to and move along respective DNA strands represented by other ones of said objects;
    a third subset of said signals comprising RNAP position signals representing physical positions of said RNAP complexes on said respective DNA strands; and
    said simulation procedure including instructions for determining movement reaction probabilities for each RNAP object in said list that represents a RNAP complex bound to a respective DNA strand, for selecting when to simulate movement of said RNAP complexes represented by said RNAP objects in accordance with said movement reaction probabilities, and for simulating movement of said RNAP complexes represented by said RNAP objects by updating said RNAP position signals.

11. The biochemical network simulator of claim 9,
    wherein a subset of said objects comprise objects representing stochastic reaction mechanisms;
    said simulation procedure including instructions for determining reaction probabilities for said objects representing stochastic reaction mechanisms, for selecting in a stochastic manner, based on said reaction probabilities, simulation times at which to simulate performance of stochastic reactions associated with said stochastic reaction mechanisms, and for simulating performance of said stochastic reactions at said selected simulation times;

said simulation procedure including instructions for updating signals associated with said objects representing stochastic reaction mechanisms, and recomputing said reaction probabilities for said objects representing stochastic reaction mechanisms based on said updated signals.

12. The biochemical network simulator of claim 11, wherein a subset of said objects comprise objects representing continuous, macroscopic reactions; and said simulation procedure including instructions for simulating said continuous, macroscopic reactions, and for updating signals associated with said objects representing said continuous, macroscopic reactions.

13. A genetic network simulator for simulating the operation of a biochemical network having a multiplicity of biochemical mechanisms, comprising:

a central processing unit;

a computer memory, coupled to said central processing unit, for storing data representing said biochemical mechanisms in said genetic network, said stored data including a set of objects, each object representing a biochemical reaction or mechanism in said biochemical network;

said stored data including, for each of at least a subset of said objects, one or more signals associated with said each object; a first subset of said signals representing quantities or concentrations of associated proteins; said stored data further including output signal designations designating a second subset of said signals as output signals;

a simulation procedure, executed by said central processing unit, that simulates operation of said biochemical network by (1) determining reaction probabilities for at least a subset of said biochemical reactions associated with said objects, (2) selecting ones of said biochemical reactions to simulate in accordance with said determined reaction probabilities, (3) simulating performance of said selected ones of said biochemical reactions, wherein simulating performance of said selected ones of said biochemical reactions causes associated ones of said signals to be updated, and (4) redetermining said reaction probabilities in accordance with said updated signals; and an output procedure, executed by said central processing unit, for generating output data representing signal values for ones of said output signals.

14. The biochemical network simulator of claim 13, wherein a subset of said objects comprise RNAP objects that represent RNAP complexes that bind to and move along respective DNA strands represented by other ones of said objects;

a third subset of said signals comprising RNAP position signals representing physical positions of said RNAP complexes on said respective DNA strands; and said simulation procedure including instructions for determining movement reaction probabilities for each RNAP object in said list that represents a RNAP complex bound to a respective DNA strand, for selecting when to simulate movement of said RNAP complexes represented by said RNAP objects in accordance with said movement reaction probabilities, and for simulating movement of said RNAP complexes represented by said RNAP objects by updating said RNAP position signals.

15. The biochemical network simulator of claim 13, wherein a subset of said objects comprise objects representing stochastic reaction mechanisms;

said simulation procedure including instructions for determining reaction probabilities for said objects representing stochastic reaction mechanisms, for selecting in a stochastic manner, based on said reaction probabilities, simulation times at which to simulate performance of stochastic reactions associated with said stochastic reaction mechanisms, and for simulating performance of said stochastic reactions at said selected simulation times;

said simulation procedure including instructions for updating signals associated with said objects representing stochastic reaction mechanisms, and recomputing said reaction probabilities for said objects representing stochastic reaction mechanisms based on said updated signals.

16. The biochemical network simulator of claim 15, wherein a subset of said objects comprise objects representing continuous, macroscopic reactions; and said simulation procedure including instructions for simulating said continuous, macroscopic reactions, and for updating signals associated with said objects representing said continuous, macroscopic reactions.

* * * * *